(12) United States Patent
Chopra et al.

(10) Patent No.: US 8,591,868 B2
(45) Date of Patent: Nov. 26, 2013

(54) SINGLE PHASE WHITENING DENTIFRICE

(75) Inventors: Suman K. Chopra, Dayton, NJ (US);
Lynette Zaidel, Cranford, NJ (US);
Michael Prencipe, West Windsor, NJ (US)

(73) Assignee: Colgate-Palmolive Company, New York, NY (US)

(*) Notice: Subject to any disclaimer, the term of this patent is extended or adjusted under 35 U.S.C. 154(b) by 81 days.

(21) Appl. No.: 13/296,282

(22) Filed: Nov. 15, 2011

(65) Prior Publication Data

US 2012/0058059 A1   Mar. 8, 2012

Related U.S. Application Data

(62) Division of application No. 11/236,082, filed on Sep. 27, 2005.

(51) Int. Cl.
*A61K 8/22* (2006.01)
*A61K 8/90* (2006.01)
*A61K 8/33* (2006.01)
*A61K 8/40* (2006.01)
*A61Q 11/00* (2006.01)

(52) U.S. Cl.
USPC .............................................. 424/53; 424/49

(58) Field of Classification Search
USPC ..................................... 424/53, 55
See application file for complete search history.

(56) References Cited

U.S. PATENT DOCUMENTS

| | | |
|---|---|---|
| 2,667,473 A | 1/1954 | Morner et al. |
| 2,938,017 A | 5/1960 | Grosser |
| 2,947,633 A | 8/1960 | Perry et al. |
| 3,306,881 A | 2/1967 | Grosser et al. |
| 3,306,886 A | 2/1967 | Grosser et al. |
| 3,577,521 A * | 5/1971 | Scheller et al. ............ 424/55 |
| 3,759,880 A | 9/1973 | Hoffmann et al. |
| 3,992,562 A | 11/1976 | Denzinger et al. |
| 4,013,285 A | 3/1977 | Green et al. |
| 4,013,825 A | 3/1977 | Denzinger et al. |
| 4,038,257 A | 7/1977 | Suzuki et al. |
| 4,136,250 A | 1/1979 | Mueller et al. |
| 4,224,427 A | 9/1980 | Mueller et al. |
| 4,250,322 A | 2/1981 | Efimov et al. |
| 4,276,402 A | 6/1981 | Chromecek et al. |
| 4,277,595 A | 7/1981 | Deichert et al. |
| 4,341,889 A | 7/1982 | Deichert et al. |
| 4,423,099 A | 12/1983 | Mueller et al. |
| 4,485,089 A | 11/1984 | Leipold |
| 4,543,398 A | 9/1985 | Bany et al. |
| 4,564,514 A | 1/1986 | Drauz et al. |
| 4,568,540 A | 2/1986 | Asano et al. |
| 4,788,052 A | 11/1988 | Ng et al. |
| 4,837,008 A | 6/1989 | Rudy et al. |
| 4,891,211 A | 1/1990 | Winston |
| 4,897,258 A | 1/1990 | Rudy et al. |
| 4,971,782 A | 11/1990 | Rudy et al. |
| 4,986,981 A | 1/1991 | Glace et al. |
| 4,988,500 A * | 1/1991 | Hunter et al. .................. 424/53 |
| 5,008,093 A | 4/1991 | Merianos |
| 5,008,106 A * | 4/1991 | Merianos et al. .......... 424/78.06 |
| 5,077,047 A | 12/1991 | Biss et al. |
| 5,108,742 A | 4/1992 | Merianos |
| 5,122,370 A | 6/1992 | Merianos et al. |
| 5,130,124 A | 7/1992 | Merianos et al. |
| 5,310,563 A | 5/1994 | Curtis et al. |
| 5,312,619 A | 5/1994 | Shih et al. |
| 5,374,368 A | 12/1994 | Hauschild |
| 5,424,060 A | 6/1995 | Hauschild |
| 5,425,953 A | 6/1995 | Sintov et al. |
| 5,496,542 A | 3/1996 | Hauschild |
| 5,614,174 A | 3/1997 | Hsu et al. |
| 5,624,906 A * | 4/1997 | Vermeer ........................ 514/23 |
| 5,676,933 A | 10/1997 | Hauschild |
| 5,718,886 A | 2/1998 | Pellico |
| 5,766,574 A | 6/1998 | Christina-Beck et al. |
| 5,776,435 A | 7/1998 | Gaffar et al. |
| 5,885,555 A | 3/1999 | Sheehan |
| 5,945,032 A | 8/1999 | Breitenbach et al. |
| 5,955,552 A | 9/1999 | Sojka |
| 6,083,421 A | 7/2000 | Huang et al. |
| 6,221,341 B1 | 4/2001 | Montgomery |

(Continued)

FOREIGN PATENT DOCUMENTS

| | | |
|---|---|---|
| CA | 2484372 | 3/2006 |
| DE | 2365631 | 10/1975 |

(Continued)

OTHER PUBLICATIONS

BASF, "Pluraflo L1220 Dispersant". Technical Bulletin from BASF Corporation copyright 2002. Printed Oct. 9, 2012.*
weiku.com, "Polypropylene-Polyoxyethylene Block Copolymer (106392-12-5)." http://www.wieku.com/chemicals/106392-12-5.html. Printed Oct. 9, 2012.*
Cabot Corporation, Product Information for Cab-o-sil® M-5, 2004.
International Search Report and Written Opinion in International Application No. PCT/US06/035278, mailed Feb. 12, 2007.
International Specialty Products, "Applications-Toothpaste and Moutbsvash," ISP Polymers for Oral Care, 2003, 10 pgs.

(Continued)

*Primary Examiner* — Walter Webb
(74) *Attorney, Agent, or Firm* — Howard C. Lee

(57) ABSTRACT

The invention provides a single phase whitening dentifrice that includes (i) a whitening agent selected from the group consisting of hydrogen peroxide, a bound peroxide and a solid peroxide (ii) an abrasive and (iii) a substantially anhydrous orally acceptable carrier, for example, polyethylene glycol. The bound peroxide may be hydrogen peroxide and a polymer and/or any peroxide compound and a porous cross-linked polymer, such as polymers of polyvinyl pyrrolidone, polyacrylates, a polymethacrylates, and a polyitaconates. The solid peroxide may be sodium perborate or urea peroxide. The invention also provides methods of whitening the tooth surfaces by contacting the surface with the composition.

16 Claims, No Drawings

(56) References Cited

U.S. PATENT DOCUMENTS

| | | |
|---|---|---|
| 6,228,385 B1 | 5/2001 | Shick |
| 6,231,848 B1 | 5/2001 | Breitenbach et al. |
| 6,277,066 B1 | 8/2001 | Irwin |
| 6,290,933 B1 | 9/2001 | Durga et al. |
| 6,331,291 B1 | 12/2001 | Glace et al. |
| 6,387,392 B1 | 5/2002 | Saito et al. |
| 6,387,995 B1 | 5/2002 | Sojka |
| 6,447,757 B1 | 9/2002 | Orlowski et al. |
| 6,514,484 B2 | 2/2003 | Rajaiah et al. |
| 6,514,543 B2 | 2/2003 | Montgomery |
| 6,555,020 B1 | 4/2003 | Chadwick et al. |
| 6,576,227 B1 | 6/2003 | Montgomery |
| 6,682,772 B1 | 1/2004 | Fox et al. |
| 6,685,921 B2 | 2/2004 | Lawlor |
| 2002/0006386 A1 | 1/2002 | Ibsen et al. |
| 2003/0124065 A1 | 7/2003 | Majeti et al. |
| 2003/0198604 A1 | 10/2003 | Lawlor |
| 2003/0206874 A1 | 11/2003 | Doyle et al. |
| 2003/0211051 A1 | 11/2003 | Majeti et al. |
| 2003/0228339 A1 | 12/2003 | El-Nokaly et al. |
| 2003/0235549 A1 | 12/2003 | Singh et al. |
| 2004/0024110 A1 | 2/2004 | Hamersky et al. |
| 2004/0086468 A1 | 5/2004 | Prosise et al. |
| 2004/0241110 A1 | 12/2004 | Lee |
| 2005/0008584 A1 | 1/2005 | Montgomery |
| 2005/0036956 A1 | 2/2005 | Fei et al. |
| 2005/0038181 A1 | 2/2005 | Chopra et al. |
| 2005/0063923 A1 | 3/2005 | Prencipe et al. |
| 2006/0045854 A1 | 3/2006 | Zaidel et al. |
| 2006/0062744 A1 | 3/2006 | Lokken |
| 2007/0071695 A1 | 3/2007 | Chopra et al. |
| 2007/0253916 A1 | 11/2007 | Maitra et al. |

FOREIGN PATENT DOCUMENTS

| | | |
|---|---|---|
| EP | 0417971 | 3/1991 |
| EP | 0535816 | 4/1993 |
| GB | 1205325 | 9/1970 |
| GB | 1443715 | 7/1976 |
| JP | 60-233110 A2 | 11/1985 |
| JP | 61-009424 A | 1/1986 |
| JP | 61-030566 A | 2/1986 |
| JP | 1030566 A | 2/1989 |
| JP | 9-040539 A | 2/1997 |
| JP | 10-305666 A | 11/1998 |
| TW | 200621299 A | 7/2006 |
| WO | WO 91/07184 | 5/1991 |
| WO | WO 01/51012 | 7/2001 |
| WO | WO 02/34221 | 5/2002 |
| WO | WO 02/072050 | 9/2002 |
| WO | WO 02/074274 | 9/2002 |
| WO | WO 03/024415 | 3/2003 |
| WO | WO 03/094877 | 11/2003 |
| WO | WO 2005/018591 | 3/2005 |
| WO | WO 2005/070378 | 8/2005 |
| WO | WO 2005/097053 | 10/2005 |
| WO | WO 2006/026424 | 3/2006 |
| WO | WO 2006/073822 | 7/2006 |

OTHER PUBLICATIONS

International Specialty Products, "Product and Applications Guide," ISP Polymers for Oral Care, 2003, 19 pgs.
Porras et al., 2004, "Studies of Formation of W/O Nano-Emulsions," Colloids and Surfaces A: Physiochem, Eng. Aspects 249:115-118.
Spindler et al., 2002, "Poly-Pore Microparticle Delivery System, A Multifunctional Delivery System for Personal Care Products," Cosmetics and Toiletries Manufacture Worldwide, 2002, 4 pgs.

* cited by examiner

SINGLE PHASE WHITENING DENTIFRICE

CROSS-REFERENCE TO RELATED APPLICATIONS

The present application is a divisional application of U.S. patent application Ser. No. 11/236,082, filed on Sep. 27, 2005, the entirety of which is hereby incorporated by reference.

BACKGROUND OF THE INVENTION

Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as smoking or other oral use of tobacco products, and eating, chewing or drinking certain foods and beverages (in particular coffee, tea and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

There are a variety of compositions described in the art for preventing or treating the discoloration of teeth. In particular, to combat staining and brighten or restore the natural enamel color, a variety of products containing bleaching materials are commercially available for professional and consumer use. The materials most commonly used in teeth whitening today are peroxides. Peroxides are generally deemed safe from a physiological standpoint, and can be effective to whiten teeth.

Professional dental treatments frequently include a tooth surface preparation such as acid etching followed by the application of highly concentrated bleaching solutions (e.g., up to 37% hydrogen peroxide) and/or the application of heat or light. These procedures provide rapid results, but are expensive, and often require several trips to the dentist. Alternatively, at-home bleaching systems can be used. These systems have gained significant popularity in the past decade because of reduced cost, and increased convenience. Instead of time consuming and frequent trips to the dentist, the tooth whitener is purchased at a consumer retail store and may be easily integrated into the daily hygiene program. At-home treatment methods include whitening strips, abrasive toothpastes, and toothpastes that contain peroxides. These peroxide toothpastes require the use of a dual chamber system that separates the peroxide from other ingredients. If the contents of the two chambers are mixed prematurely, the oxidation activity and whitening benefits are lost.

It would be desirable to provide a whitening oral care composition which promotes consumer compliance and utilizes a single chamber or tube to deliver sufficient amounts of whitening ingredients and other oral care actives without adverse reaction between the ingredients.

BRIEF SUMMARY OF THE INVENTION

The invention provides a single phase whitening dentifrice that includes (i) a whitening agent selected from the group consisting of hydrogen peroxide, a bound peroxide and a solid peroxide (ii) an abrasive and (iii) a substantially anhydrous orally acceptable carrier, for example, polyethylene glycol. The bound peroxide may be hydrogen peroxide and a polymer and/or any peroxide compound and a porous cross-linked polymer, such as polymers of polyvinylpyrrolidone, polyacrylates, a polymethacrylates, and a polyitaconates. The solid peroxide may be sodium perborate or urea hydroxide.

The invention also provides methods of whitening the tooth surfaces by contacting the surface with the composition.

DETAILED DESCRIPTION OF THE INVENTION

The present invention provides single phase whitening oral care compositions, comprising a peroxide whitening agent; a peroxide incompatible abrasive; and a substantially anhydrous orally acceptable carrier. In various embodiments, the substantially anhydrous orally acceptable carrier and the particular peroxides employed allow for a shelf-stable single tube oral care composition where the peroxide and the peroxide incompatible ingredients, such as abrasives, may be combined. The oral care composition provides highly efficacious whitening and cleaning.

The single phase oral care composition has a "low water" content, meaning that a total concentration of water, including any free water and all water contained in any ingredients, is less than about 4%, about 7% or less than about 10% water. The selection of the whitening agent in conjunction with the low water carrier provides stabilized delivery of the whitening agent. The whitening activity is maintained for application to the tooth or oral surface and is maintained through storage.

Any whitening agent known or developed in the art may be used. Preferably, the whitening agent includes solid whitening agents and bound whitening agents which are substantially anhydrous oxygen generating compounds. Solid whitening agents useful herein include peroxides, metal chlorites, persulfate. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. Suitable metal chlorites include calcium chlorite, barium chlorite, magnesium chlorite, lithium chlorite, sodium chlorite, and potassium chlorite. The whitening agent may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some embodiments, it may be desirable to use any known whitening agent except sodium percarbonate and/or any of the percarbonate salts.

The compositions of the present invention may include any dental abrasive or combination of dental abrasive agents known or to be developed in the art. "Abrasive" is as used herein is meant to include materials commonly referred to as "polishing agents" as well. Suitable abrasive may include those previously considered to be incompatible in a peroxide containing formulation ("a peroxide-incompatible abrasive"). Such abrasive is one which, in an aqueous solution with hydrogen peroxide, substantially reacts with the hydrogen peroxide so as to reduce whitening efficacy of the solution.

Any orally acceptable abrasive can be used, but preferably, type, fineness (particle size) and amount of abrasive should be selected so that tooth enamel is not excessively abraded in normal use of the composition. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, (3-calcium pyrophosphate, tricalcium phosphate, calcium polymetaphosphate and insoluble sodium polymetaphosphate. Average particle size of an abrasive, if present, is generally about 0.1 to about 30 μm, for example about 1 to about 20 μm or about 5 to about 15 μm. One or more abrasives are present in an abrasive effective total amount, typically about 0.1% to about 40%.

In various embodiments of the present invention, the oral composition comprises an anticalculus agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The anticalculus agent is present at about 0.1% to about 30%. The oral composition may include a mixture of different anticalculus agents. In one preferred embodiment, tetrasodium pyrophosphate (TSPP) and sodium tripolyphosphate (STPP) are used. The anticalculus agent comprises TSPP at about 1% and STPP at about 7% to about 10%.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions.

The carrier is preferably low water content orally acceptable carrier and may include any known ingredients or additives.

In preferred embodiments of this invention, the oral composition is a dentifrice. Such dentifrices may include toothpowder, a dental tablet, toothpaste (dental cream), tooth powders, or gel, or any other known form known to one of skill in the art.

The substantially anhydrous carrier may also comprise various dentifrice ingredients to adjust the rheology and feel of the composition such as humectants, surface active agents, thickening or gelling agents, etc.

The compositions of the present invention preferably comprise a surface active agent. Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

The compositions of the present invention optionally comprise a thickener. Any orally acceptable thickening agent can be used, including without limitation carbomers, also known as carboxyvinyl polymers, carrageenans, also known as Irish moss and more particularly i-carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

In various preferred embodiments, the carrier may comprise polymers and/or copolymers of polyethylene glycol, of ethylene oxide propylene oxide, and of silicone. IF such copolymers/polymers are used, they may be selected from the commercially available materials PLURAFLO® L4370 and PLURAFLO® L1220 (available from BASF, Wyandotte, Mich., United States of America). It is preferred that the carrier(s) provide a dentifrice with a viscosity of about 10,000 CPS to about 700,000 CPS, preferably about 30,000 CPS to about 300,000 CPS.

As recognized by one of skill in the art, the oral compositions of the present invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention optionally comprise one or more further active material(s), which is operable for the prevention or treatment of a condition or disorder of hard or soft tissue of the oral cavity, the prevention or treatment of a physiological disorder or condition, or to provide a cosmetic benefit.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The compositions of the present invention optionally comprise an antimicrobial (e.g., antibacterial) agent. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialagogue or saliva-stimulating agent, an antiplaque agent, an anti-inflammatory agent, a desensitizing.

Methods are provided to whiten an oral surface in a human or animal subject comprising storing in stable form a whitening oral care composition comprising a peroxide whitening agent, a peroxide incompatible abrasive, and a substantially anhydrous and a substantially anhydrous orally acceptable carrier; and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The invention is illustrated in the following non-limiting examples.

EXAMPLES

Comparative Example I

A comparative, non-abrasive containing single phase dentifrice is prepared by mixing the ingredients of Table 1. After aging the dentifrice for two weeks at approximately 49° C., the peroxide recovery was 89% of the initially present amount.

TABLE 1

| Ingredients | Weight Percentage |
| --- | --- |
| Cross-linked polyvinyl pyrrolidone - hydrogen peroxide complex | 16.50 |
| Polyethylene Glycol/Ethylene Oxide Copolymer (PLURAFLO ® L4370) | 42.44 |
| Ethylene Oxide/Propylene Oxide Copolymer (PLURAFLO ® L1220) | 25.00 |
| Silicone fluid | 5.00 |
| Saccharin | 0.42 |
| Flavor | 1.20 |
| Tetrasodium pyrophosphate | 1.00 |
| Sodium tripolyphosphate | 7.00 |
| Sodium fluoride | 0.24 |
| Sodium lauryl sulfate | 1.20 |
| TOTAL | 100.00 |

Example 1

A single phase dentifrice was prepared by mixing the ingredients of Table 2. A peroxide incompatible silica abrasive is included at 12.44% and increases the cleaning and whitening benefits of the dentifrice. After aging the dentifrice for two weeks at approximately 49° C., the peroxide recovery was 77% of the initially present amount.

TABLE 2

| Ingredients | Weight Percentage |
| --- | --- |
| Cross-linked polyvinyl pyrrolidone - hydrogen peroxide complex | 16.50 |
| Polyethylene Glycol/Ethylene Oxide Copolymer (PLURAFLO ® L4370) | 30.00 |
| Ethylene Oxide/Propylene Oxide Copolymer (PLURAFLO ® L1220) | 25.00 |
| Silicone fluid | 5.00 |
| Saccharin | 0.42 |
| Flavor | 1.20 |
| Tetrasodium pyrophosphate | 1.00 |
| Sodium tripolyphosphate | 7.00 |
| Sodium fluoride | 0.24 |
| Silica abrasive | 12.44 |
| Sodium lauryl sulfate | 1.20 |
| TOTAL | 100.00 |

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

We claim:

1. A single phase oral care composition, comprising:
    a peroxide whitening agent comprising a complex of hydrogen peroxide and cross-linked polyvinylpyrrolidone;
    an abrasive wherein the abrasive is selected from the group consisting of calcium pyrophosphate; calcium carbonate; and dicalcium phosphate;
    an anticalculus agent; and
    a substantially anhydrous carrier;
    wherein the carrier comprises an ethylene oxide/propylene oxide copolymer.

2. The composition of claim 1, wherein the abrasive is calcium carbonate.

3. The composition of claim 1, wherein the anticalculus agent comprises an agent selected from: a polyphosphate; a hexametaphosphate salt; a polyolefin sulfonate; and a combination of two or more thereof.

4. The composition of claim 1, wherein the carrier has a total water content of less than about 4%, by weight.

5. The composition of claim 1, wherein the composition is a dentifrice.

6. The composition of claim 1, wherein the abrasive comprises calcium pyrophosphate.

7. The composition of claim 1, wherein the abrasive is dicalcium phosphate.

8. The composition of claim 2, wherein the anticalculus agent comprises an agent selected from: a polyphosphate; a hexametaphosphate salt; a polyolefin sulfonate; and a combination of two or more thereof.

9. The composition of claim 6, wherein the anticalculus agent comprises an agent selected from: a polyphosphate; a hexametaphosphate salt; a polyolefin sulfonate; and a combination of two or more thereof.

10. The composition of claim 7, wherein the anticalculus agent comprises an agent selected from: a polyphosphate; a hexametaphosphate salt; a polyolefin sulfonate; and a combination of two or more thereof.

11. The composition of claim 8, wherein the carrier has a total water content of less than about 4%, by weight.

12. The composition of claim 9, wherein the carrier has a total water content of less than about 4%, by weight.

13. The composition of claim 10, wherein the carrier has a total water content of less than about 4%, by weight.

14. The composition of claim 11, wherein the composition further comprises sodium lauryl sulfate and a fluoride source.

15. The composition of claim 12, wherein the composition further comprises sodium lauryl sulfate and a fluoride source.

16. The composition of claim 13, wherein the composition further comprises sodium lauryl sulfate and a fluoride source.

* * * * *